United States Patent
Hegland

(10) Patent No.: US 10,357,334 B2
(45) Date of Patent: Jul. 23, 2019

(54) DENTAL DEVICES AND METHODS FOR TREATING ONE OR MORE TEETH

(71) Applicant: Hegland LLC, Clearwater, MN (US)

(72) Inventor: Lindsay Hegland, Clearwater, MN (US)

(73) Assignee: Hegland LLC, Plymouth, MN (US)

( * ) Notice: Subject to any disclaimer, the term of this patent is extended or adjusted under 35 U.S.C. 154(b) by 760 days.

(21) Appl. No.: 14/140,836

(22) Filed: Dec. 26, 2013

(65) Prior Publication Data

US 2015/0182301 A1 Jul. 2, 2015

(51) Int. Cl.
*A61C 5/85* (2017.01)
*A61C 19/06* (2006.01)
*A61C 9/00* (2006.01)
*A61C 13/00* (2006.01)
*A61C 13/15* (2006.01)

(52) U.S. Cl.
CPC .............. *A61C 5/85* (2017.02); *A61C 19/066* (2013.01); *A61C 9/0053* (2013.01); *A61C 13/0004* (2013.01); *A61C 13/0013* (2013.01); *A61C 19/004* (2013.01)

(58) Field of Classification Search
CPC ..... A61C 5/125; A61C 19/066; A61C 9/0053; A61C 13/0004; A61C 13/0013; A61C 19/004; A61C 8/0001; A61C 13/34; A61C 5/85; Y10T 29/49567
USPC .................................................. 433/39, 213
See application file for complete search history.

(56) References Cited

U.S. PATENT DOCUMENTS

| | | | | |
|---|---|---|---|---|
| 2,094,308 A | * | 9/1937 | Snell | A61C 9/00 205/70 |
| 2,674,801 A | * | 4/1954 | Trangmar | A61C 5/85 433/39 |
| 2,790,238 A | * | 4/1957 | Trangmar | A61C 5/85 29/896.1 |
| 4,611,288 A | | 9/1986 | Duret | |
| 6,482,005 B1 | * | 11/2002 | Summer | A61C 5/85 433/39 |
| 6,766,217 B1 | * | 7/2004 | Hamada | A61C 5/00 700/163 |

(Continued)

OTHER PUBLICATIONS

Quercus Corporation, "Temporary Crown Restorations," 2nd edition, 64 pages, copyright 1979, updated 1991, revised Jun. 2005.

*Primary Examiner* — Heidi M Eide
*Assistant Examiner* — Mirayda A Aponte
(74) *Attorney, Agent, or Firm* — Fish & Richardson P.C.

(57) ABSTRACT

A dental device (such as a dental matrix or teeth tray) for use in in securing to one or more teeth during a dental restoration procedure or another dental procedure. In the case of a dental matrix, the dental matrix can be manufactured (e.g., in a dentist's facility using a three-dimensional printer apparatus or the like) after the targeted tooth of the patient in the dentist's facility is prepared for a filling material. As such, in some circumstances, the dental matrix is not necessarily a prefabricated metal band that is intended to be used with any of a variety of differently sized and shaped teeth of any of a variety of different patients, but instead the dental matrix may optionally be promptly fabricated according to the specific anatomical shape and size of a particular tooth of a particular patient while that patient is waiting in the dental chair.

18 Claims, 10 Drawing Sheets

(56) References Cited

U.S. PATENT DOCUMENTS

| | | | |
|---|---|---|---|
| 7,029,279 B2 | 4/2006 | Schomann | |
| 7,112,065 B2 | 9/2006 | Kopelman | |
| 7,442,041 B2 | 10/2008 | Imgrund | |
| 7,458,812 B2 | 12/2008 | Sporbert | |
| 7,474,932 B2 * | 1/2009 | Geng | A61C 13/0004 700/98 |
| 7,735,542 B2 | 6/2010 | Marshall | |
| 8,371,854 B2 * | 2/2013 | Ahmed | A61C 5/85 433/226 |
| D690,423 S | 9/2013 | Pieroni | |
| 8,562,339 B2 | 10/2013 | Raby | |
| 9,387,056 B2 * | 7/2016 | Wachter | A61C 13/0013 |
| 2001/0038705 A1 * | 11/2001 | Rubbert | A61C 7/00 382/128 |
| 2009/0148813 A1 * | 6/2009 | Sun | A61C 13/0001 433/201.1 |
| 2009/0191505 A1 * | 7/2009 | Clark | A61C 5/50 433/39 |
| 2009/0208896 A1 * | 8/2009 | Clark | A61C 5/50 433/39 |
| 2010/0219546 A1 * | 9/2010 | Puttler | A61C 7/00 264/16 |
| 2014/0011162 A1 * | 1/2014 | Zegarelli | A61C 13/0013 433/215 |
| 2018/0021113 A1 * | 1/2018 | Hansen | A61C 13/0004 433/213 |

* cited by examiner

DENTAL DEVICES AND METHODS FOR TREATING ONE OR MORE TEETH

TECHNICAL FIELD

The subject matter of this disclosure is related to dental devices and related methods of treating one or more teeth.

BACKGROUND

Dental caries afflicts people world-wide. Dental caries can be repaired through a process that involves removing decayed portions of a tooth and replacing the removed portions with a filling. In a typical filling process, a dentist will use a local anesthetic to numb the area around a targeted tooth to be treated. The dentist can then use a drill or laser to remove decayed portions of the tooth. The dentist can then prepare the space created in the tooth by cleaning the area of bacteria and debris, and the dentist subsequently fills the space with a filling material. Filling materials can include gold, porcelain, silver amalgam, or composite resin fillings. After filling material has been applied, the dentist can contour the tooth to a desired shape by trimming or polishing away excess material.

In some circumstances, the dentist can use a dental matrix—often in the form of a flexible metal band—that is partially bent around the tooth and temporarily retained in a selected position (e.g., using a clamp or other tool) after removal of the decayed portion but before application of the filling material. After the dental matrix band is secured to the targeted tooth, a cavity which has been prepared by the dentist can be filled with a filling material (while dental matrix band preferably reduces seepage of the filling material outside of the cavity). Due to the varying size and shape of the targeted teeth in dental patients, the dental matrix band may not be capable of being properly seated or bent around the targeted tooth, thereby permitting some of the filling material to flow outwardly beyond the cavity area (e.g., beyond the normal anatomical shape of the targeted tooth).

SUMMARY

Some embodiments of a system or method for treating one or more targeted teeth can employ a customized dental matrix that is formed according to the specific contours of a patient's mouth and teeth. For example, the dental matrix can be manufactured (e.g., in a dentist's facility using a three-dimensional printer apparatus or the like) after the targeted tooth of the patient in the dentist's facility is prepared for a filling material. As such, in some circumstances, the dental matrix is not necessarily a prefabricated metal band that is intended to be used with any of a variety of differently sized and shaped teeth of any of a variety of different patients, but instead the dental matrix may optionally be promptly fabricated according to the specific anatomical shape and size of a particular tooth of a particular patient while that patient is waiting in the dental chair. Also, in some embodiments, the customized dental matrix can comprise a flexible, biocompatible, polymer material having a number of characteristics that can add efficiencies to the dental procedures, reduce the likelihood of excessive pressure on non-anesthetized gingival tissues, and reduce the likelihood of the filling material flowing outwardly beyond the prepared cavity area. Finally, some of the systems and methods described herein are not limited to dental matrix devices, but instead can be used to provide a teeth tray (for whitening teeth, for delivering fluoride or another material to teeth, or the like) or other dental device that is customized to fit with one or more teeth of a particular patient's mouth.

Particular embodiments described herein include a system for providing a customized dental matrix. The system may include a digital imaging dental tool configured to collect digital impression data for one or more teeth positioned within a mouth of a patient. The system may also include a computer system configured to receive digital impression data from the digital imaging wand and generate a three-dimensional model of a dental matrix for a first tooth of the one or more teeth. A shape of the dental matrix may be at least partially defined to correspond to an identified shape of a portion of the first tooth. The system may further include a rapid fabrication device. Optionally, the rapid fabrication device may be configured to receive data indicative of the three-dimensional model from the computer system and fabricate the dental matrix according to the received data. The system may optionally include at least one dental matrix. The dental matrix may be fabricated by the rapid fabrication device, and the shape of the dental matrix may be defined by the three-dimensional model and corresponding to the identified shape of the portion of the first tooth.

Additional embodiments described herein include a dental matrix. The dental matrix may include a polymer material defining a matrix wall having an inner surface and an outer surface. The polymer material may optionally be transparent, as described below. The dental matrix may further provide an aperture defined by the inner surface of the matrix wall. The inner surface of the matrix wall may be shaped to correspond to one or more contours of a surface of the targeted tooth. Optionally, the dental matrix may be configured to receive the targeted tooth within the aperture so as to circumferentially encompass the targeted tooth during a dental procedure and engage the one or more contours of the surface of the targeted tooth.

In some embodiments, a method for using a dental matrix includes preparing a targeted tooth of a patient in a dental facility building for receiving a filling material. The method may also include, after preparing the targeted tooth for receiving the filling material, fabricating at a rapid fabrication device in the dental facility building a patient-specific dental matrix for insertion along the targeted tooth of the patient. The patient-specific dental matrix may be fabricated based at least in part on digital impression data for the targeted tooth of that particular patient. The method may further include inserting the patient-specific dental matrix along the targeted tooth of the patient in the dental facility building.

In other embodiments, a method for creating a customized dental matrix includes acquiring, by a computer system, digital impression data for one or more teeth positioned within a mouth of a patient. The method may also include determining, by the computer system and using the acquired digital impression data, a shape of at least a first portion of a first tooth of the one or more teeth. The method may further include generating, by the computer system, a three-dimensional model of a dental matrix for insertion along the first tooth. A shape of the dental matrix may be at least partially defined to correspond to the determined shape of the first portion of the first tooth. The method may also include transmitting, by the computer system, data representing the three-dimensional model to a rapid fabrication device for fabricating the dental matrix for insertion along the first tooth.

Further embodiments described herein include a method for curing a dental material (such as a dental filling material). The method may include positioning a dental matrix along at least one targeted tooth having a prepared cavity area. The dental matrix may be transparent, as described below. The method may also include depositing dental material within the prepared cavity area of the targeted tooth. The method may further include transmitting ultraviolet light through the transparent dental matrix such that at least a portion of the dental material is exposed to the ultraviolet light passing through the transparent dental matrix.

Some embodiments described herein include a dental matrix for adjacent teeth. The dental matrix may include a first inner surface defining a first aperture, and the first inner surface of the dental matrix may be shaped to correspond to contours of a first surface of a first tooth. The dental matrix may also include a second inner surface defining a second aperture and being a unitary structure with the first inner surface. The second inner surface of the dental matrix may be shaped to correspond to contours of a second surface of a second tooth. The dental matrix may be configured to receive the first tooth within the first aperture and the second tooth within the second aperture so as to circumferential encompass each of the first and second teeth with the dental matrix.

In some embodiments, a system for providing a patient-specific dental tray may include a digital imaging dental tool configured to collect digital impression data for targeted teeth positioned within a mouth of a patient. The system may also include a computer system configured to receive digital impression data from the digital imaging tool and generate a three-dimensional model of a dental tray for the targeted teeth. The shape of the dental tray may be at least partially defined to correspond to an identified shape of the targeted teeth. The system may further include a rapid fabrication device configured to receive data indicative of the three-dimensional model from the computer system and fabricate the dental tray according to the received data. The system may also include at least one dental tray fabricated by the rapid fabrication device, and the shape of the dental tray may be defined by the three-dimensional model and corresponding to the identified shape of the targeted teeth.

Particular embodiments described herein include a method for using a patient-specific dental tray with a set of targeted teeth. The method may include obtaining digital imaging data of targeted teeth of a patient in a dental facility building. The method may also include, after obtaining digital imaging data of the targeted teeth, fabricating at a rapid fabrication device in the dental facility building a patient-specific dental tray for mating with the targeted teeth. The patient-specific dental tray may be fabricated based at least in part on the digital imaging data of the targeted teeth of the patient. The method may further include inserting the patient-specific dental tray along the targeted tooth of the patient in the dental facility building.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
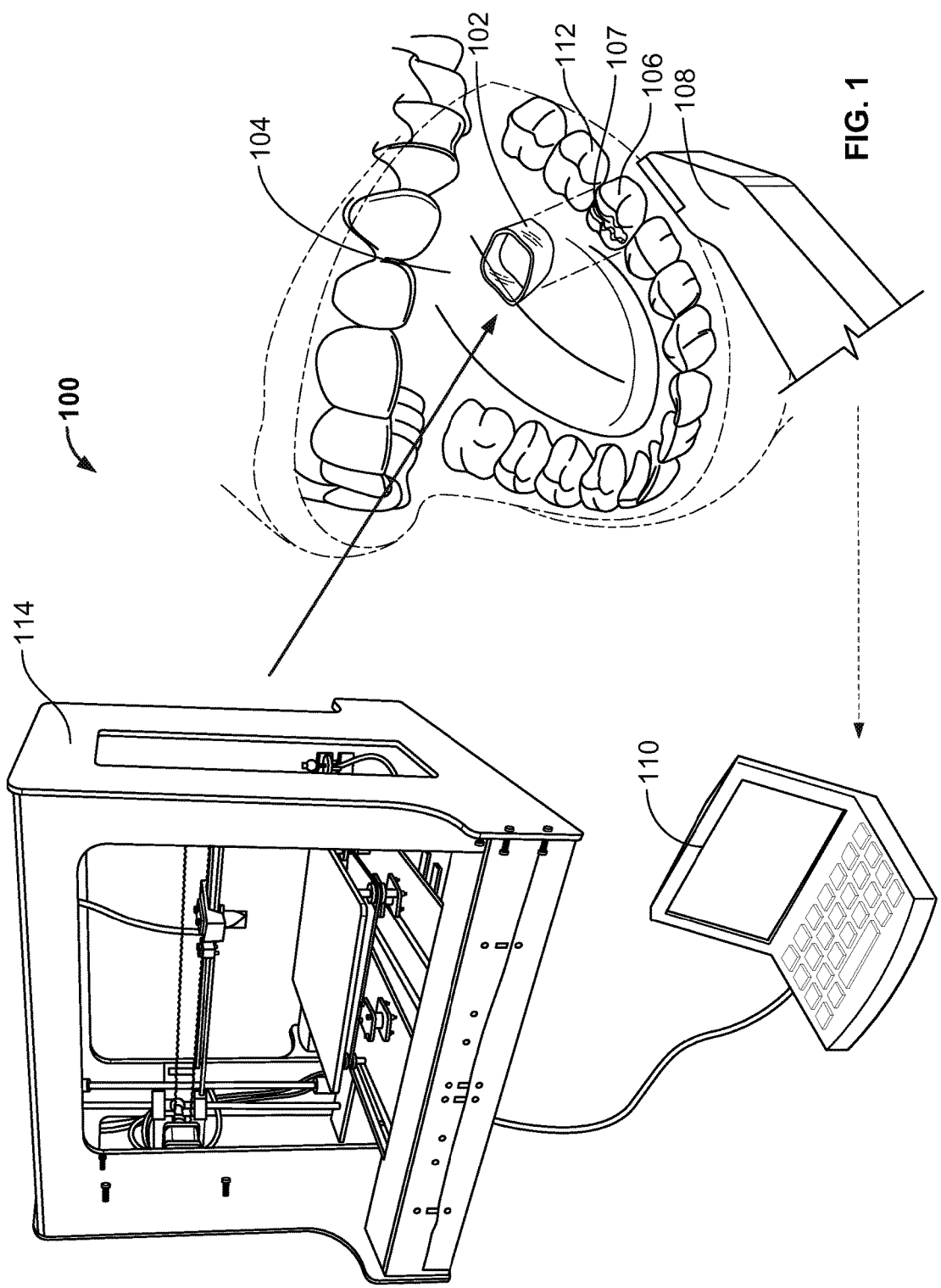
FIG. 1 shows a perspective view of a dental system, in accordance with some embodiments.

Referring to FIG. 1, some embodiments of a system 100 for treating one or more targeted teeth can employ a customized dental matrix 102 that can be formed to fit the specific contours of a particular targeted tooth 106 of a particular patient. As described in more detail below, the dental matrix 102 can be created onsite and in response to receiving digital images or another type of digital impression of the patient's teeth 106 and 112 (e.g., using a dental imaging wand 108 and a computer system 110). For example, the dental matrix 102 can be formed in an intra-office process (e.g., in a dentist's facility using a rapid fabrication machine 114 such as a three-dimensional printer apparatus or the like) after the targeted tooth 106 of the patient (located in the same dentist's facility) is prepared for a filling material (e.g., a prepared cavity area 107). In such embodiments, the dental matrix 102 is not necessarily a prefabricated metal band that is located in the inventory of the dentist's facility before the patient arrives, but instead the dental matrix 102 can be promptly fabricated according to the patient-specific anatomical shape and size of a particular tooth of a particular patient while that patient is waiting in the dental chair or in another area of the same dentist's facility. As described in more detail below, the customized dental matrix 102 can be implemented in a manner that adds efficiencies to the dental procedures (e.g., a composite resin restoration or another procedure), that reduces the likelihood of excessive pressure on non-anesthetized gingival tissues, and that provides an improved fitting to the targeted tooth 106 so that the filling material is unlikely to flow outwardly beyond the prepared cavity area 107.

Briefly, in use, the customized dental matrix 102 can be inserted into a mouth 104 of a patient during a dental procedure, such as a direct resin restoration procedure, another cavity filling procedure, or the like. In the depicted embodiments, the customized dental matrix 102 is preferably inserted into the mouth 104 such that the customized dental matrix 102 surrounds the exterior sides of the targeted tooth 106 of the patient. For example, the customized dental matrix 102 can be inserted over the targeted tooth 106 after a decayed portion has been removed (e.g., through drilling or other operations) from the targeted tooth 106. The customized dental matrix 102 can be positioned adjacent to the prepared cavity area 107 so as to at least partially define the periphery of the space for the filling material that is subsequently inserted into the prepared cavity area 107. The dental matrix 102 can be customized to fit specific contours of the targeted tooth 106 prior to delivery of the filling material, and thus the matrix 102 may take on a shape that closely or exactly matches the original shape of the targeted tooth 106. For example, in particular embodiments in which the dental matrix 102 is fabricated according to the custom size and shape of the targeted tooth 106 (examples described below), the dental matrix 102 can be used to provide an improved gingival preparation (helping to seal out sulcular fluids during the procedure and reducing the likelihood of overextending or underextending the filling material over), to provide an improved embrasure form that defines satisfactory contact points between the targeted tooth 106 and its neighboring teeth 112, and to simplify the efforts of securing the dental matrix 102 to the targeted tooth 106 (e.g., without the use of external clamp devices).

Still referring to FIG. 1, in some implementations for creating the customized dental matrix 102, a practitioner such as a dentist can use a dental imaging wand 108 to scan the targeted tooth 106 and surrounding areas of the mouth 104 to obtain imaging data for generating a three-dimensional image of the targeted tooth 106 or another type of digital impression for the targeted tooth 106. For example, the dental scanning wand 108 can take digital images of the targeted tooth 106 and surrounding areas of the mouth 104 that can be combined to create a three-dimensional Computer Aided Design (CAD) model of the targeted tooth 106. In some implementations, the entire mouth 104 or the entire lower jaw of the patient is scanned. In some implementations, it is only necessary to scan the targeted tooth 106, the teeth 112 that are adjacent to the targeted tooth 106 and gingival areas near the targeted tooth 106. In some implementations, only the targeted tooth 106 is scanned using the dental imaging wand 108.

The dental imaging wand 108 can be connected to a computer system 110 so that the wand 108 is configured to transmit the captured imaging data to the computer system 110 for further processing. The dental scanning wand 108 can transmit information to the computer system 110 through wireless or wired communications. The computer system 110 can be, for example, a desktop or portable computer located in a dentist's office, a group of computers in communication with each other, or a remote computer in communication with a computing apparatus attached to the dental imaging wand 108 through a network. The computer system 110 can use digital imaging information captured by the dental imaging wand 108 to create a three-dimensional digital image of the targeted tooth 106 and areas of the mouth 104 in close proximity to the targeted tooth 106 (sometimes referred to as a digital dental impression). Software running on the computer system 110 can then use the three-dimensional digital image of the targeted tooth 106 to generate a CAD model for fabricating the customized dental matrix 102. The computer system 110 can generate the CAD model such that the customized dental matrix 102 defined by the CAD model is shaped to match contours of the targeted tooth 106 (including the contours of the cervical-third) and to define satisfactory embrasure forms with the neighboring tooth 112. For example, the CAD model defines a shape for the inner surfaces of the customized dental matrix 102 such that the inner surfaces of the customized dental matrix 102 conform to the contours of the targeted tooth 106 when the customized dental matrix 102 is inserted over the targeted tooth 106 (refer to FIGS. 4 and 9B for some examples).

In some implementations, the CAD model defines portions of the outer surfaces of the customized dental matrix 102 to engage teeth and gums in close proximity to the targeted tooth 106 in a patient-specific, customized manner. For example, the dental imaging wand 108 can capture digital images of at least a portion of the neighboring tooth 112 that is positioned next to the targeted tooth 106 (or both of the neighboring teeth 112). The computer system 110 can use the digital information captured by the dental scanning wand 108 to generate the CAD model such that a portion of the outer surface of the customized dental matrix 102 is custom shaped to conform to the contours of a proximal surface of the tooth 112 that faces the targeted tooth 106. Such contour shaping of the outer surface of the customized dental matrix 102 can be used to define preferred embrasure forms between the teeth 106 and 112 and to provide proper spacing between the targeted tooth 106 and the neighboring tooth 112 is maintained when filling material is deposited at the targeted tooth 106.

Still referring to FIG. 1, in some embodiments of the system 100, the computer system 110 can be in electronic communication with rapid fabrication machine 114 such as a three-dimensional printer. For example, in the depicted embodiment, the computer system 110 can use the generated CAD model of the customized dental matrix 102 to transmit instructions to the three-dimensional printer 114 for fabricating the customized dental matrix 102. The three-dimensional printer 114 creates the customized dental matrix 102 by depositing or solidifying layers of material until a three-dimensional structure defined by the CAD model is complete. In some implementations, the three-dimensional printer 114 is located locally in the dentist's facility (e.g., within the walls of the dentist's facility while the patient is waiting within the same dentist's facility). When the three-dimensional printer 114 is located locally in the dentist's facility, the system 100 can be used to create a digital impression of the patient's mouth 104, fabricate the customized dental matrix 102, and apply the filling material to the prepared cavity site 107 of the targeted tooth 106 all in one office visit.

In some alternative implementations, the three-dimensional printer 114 can be located remotely and the generated CAD model or other digital information used in creating the customized dental matrix 102 can be transmitted from the computer system 110 to the three-dimensional printer 114 through a network (e.g., the Internet). In such scenarios, after the customized dental matrix 102 has been fabricated at the remote three-dimensional printer 114, the customized dental matrix 102 can be delivered to the dentist's office (e.g., by a courier service or another agent) for use during a dental filling procedure.

Still referring to FIG. 1, the three-dimensional printer 114 can be configured to fabricate the dental matrix 102 so that the resulting product comprises a flexible, biocompatible, polymer material. In some implementations, the customized dental matrix 102 can comprise a transparent material (i.e., sufficiently transparent so as to permit passage of a UV curing light through the body of the dental matrix 102 and toward the targeted tooth 106). As described in more detail below, the customized dental matrix 102 can be formed as a transparent or semi-transparent structure for purposes of permitting UV rays from a dental curing light to transmit through the customized dental matrix 102 to cure filling material during a curing process of a direct resin restoration procedure or the like.

For example, after the customized dental matrix 102 has been created, the customized dental matrix 102 is inserted into the mouth 104 such that the customized dental matrix 102 snugly fits around the targeted tooth 106 and engages the patient-specific contours of the targeted tooth 106 (including the cervical-third, or lower ⅓, of the tooth near the gingival tissue). After the customized dental matrix 102 is inserted over the targeted tooth 106, the prepared cavity area 107 can be etched, rinsed, treated with a bond fluid (which is cured via a UV light in some embodiments), and then filled with the filling material (e.g., composite resin material that is cured via a UV light in some embodiments).

In this example, the bond fluid and then the filling material are cured by emitting UV light on the bond fluid or the filling material using a dental curing light. Because the customized dental matrix 102 in this embodiment is created using a transparent material, the UV light can transmit through the body of customized dental matrix 102 to cure the filling material (refer, for example, to FIGS. 5A-B). In some implementations, the filling material is deposited to prepared cavity area 107 of the targeted tooth 106 in sequential layers, with each layer being cured prior to application of a subsequent layer. As filling material is applied to the targeted tooth 106, the customized dental matrix 102 causes the filling material to take on the preferred anatomical shape of the targeted tooth 106 since the inner surfaces of the customized dental matrix 102 have been specifically tailored to conform to the selected shape that matches contours of the targeted tooth 106 (including the contours of the cervical-third) and defines satisfactory embrasure forms with the neighboring tooth 112. Also, due to the customized fit of the dental matrix 102 and its flexible properties, it can form a seal with a lower cervical rim of the targeted tooth 106 to thereby reduce the likelihood of the filling material leaking onto the gums and surrounding areas of the mouth 104 during the deposition of the filling material.

In some optional implementations, the customized dental matrix 102 can include one or more extending portions for retracting cheek tissue or the patient's tongue to maintain a clearance distance between the prepared cavity area 107 of the targeted tooth 106 and the patient's cheek, the patient's tongue, or both during a composite resin restoration procedure. For example, customized dental matrix 102 can include a buccal (cheek side) extension (or wing) that extends away from the buccal wall portion of the dental matrix 102 (and thus away from the targeted tooth 106) to retract cheek tissue away from the area over and around the targeted tooth 106. The buccal extension (not shown in FIG. 1) can be integrally formed (i.e., a unitary structure) with the dental matrix 102 at the three-dimensional printer 114 (after the computer system 110 defines the size and angular relationship of the buccal extension relative to the main body of the dental matrix 102 in response to receiving the digital imaging data). In particular examples, the buccal extension may appear as a flexible wing or flap that extends away from the buccal-most wall portion of the dental matrix 102 so as to rest against the patient's cheek when the dental matrix 102 is engaged with the targeted tooth 106. As another example, the customized dental matrix 102 can include a lingual (tongue side) extension (or wing) that extends away from the lingual wall portion of the dental matrix 102 (and thus away from the targeted tooth 106) toward the inside of the mouth 104 to retract the patient's tongue away from the area over and around the targeted tooth 106. The lingual extension (not shown in FIG. 1) can be integrally formed (i.e., a unitary structure) with the dental matrix 102 at the three-dimensional printer 114 (after the computer system 110 defines the size and angular relationship of the lingual extension relative to the main body of the dental matrix 102 in response to receiving the digital imaging data). In particular examples, the lingual extension may appear as a flexible wing or flap that extends away from the lingual-most wall portion of the dental matrix 102 so as to rest against the patient's tongue when the dental matrix 102 is engaged with the targeted tooth 106. As such, the buccal and lingual extensions can be useful for keeping the area around the prepared cavity area 107 free of cheek and tongue tissue, thereby increasing visibility for a practitioner applying filling material to the prepared cavity area 107 and furthermore reducing isolation complications such as saliva or hemorrhage.

Figure 2:
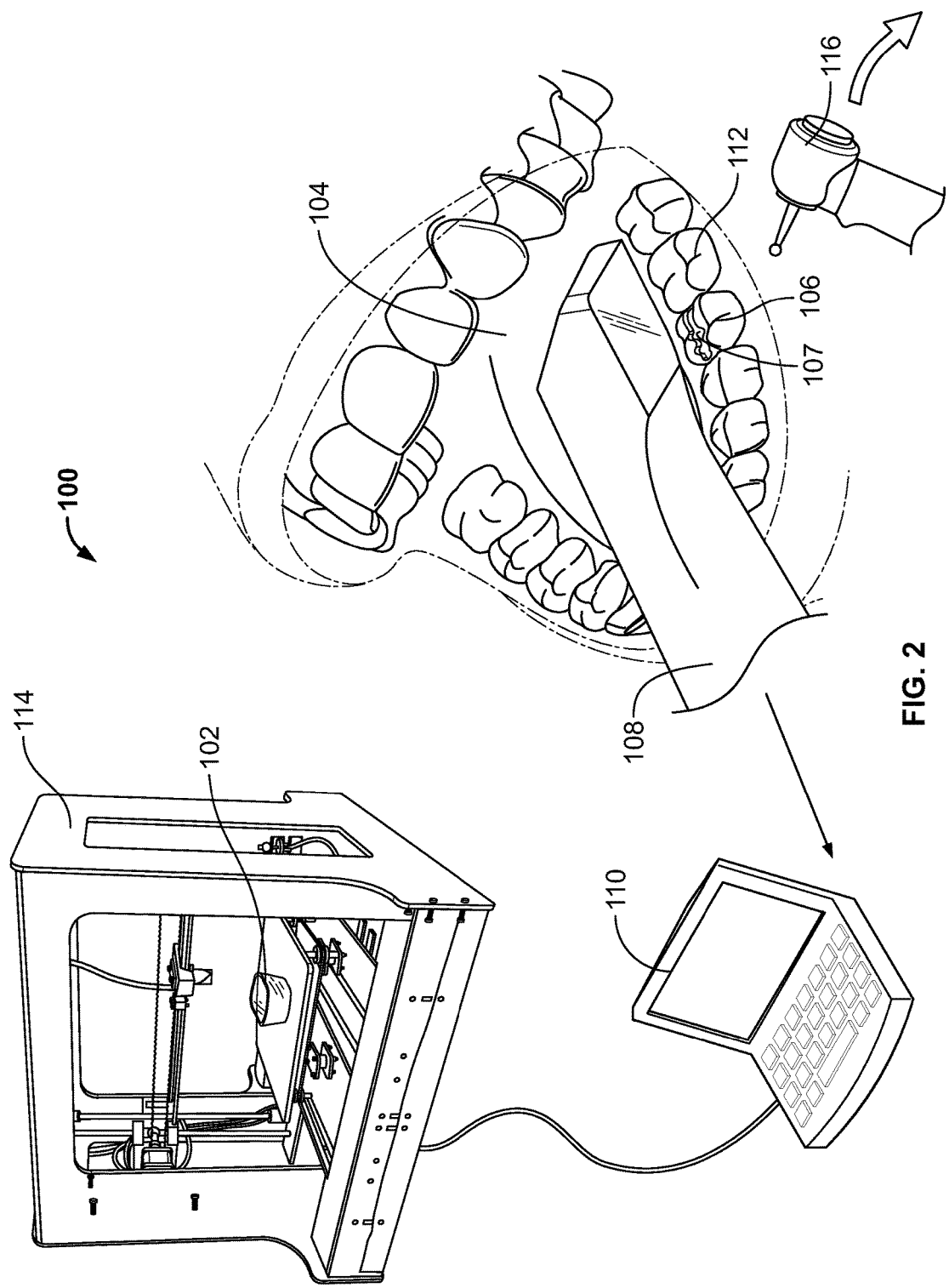
FIG. 2 shows a perspective view of the dental system of FIG. 1, including a customized dental matrix device.

Referring now to FIGS. 2-5B, some embodiments of a dental procedure can be implemented using the system 100 including the customized dental matrix 102. As shown in FIG. 2, the dental procedure can include operations of identifying and removing decayed portions of the targeted tooth 106 so as to create a prepared cavity area 107. For example, a practitioner (e.g., a dentist or another clinician) can identify decayed portions of the targeted tooth 106 and remove the decayed portions using a dental drill 116 to prepare the tooth for application of a composite resin material or other filling material. In some implementations, one or more alternative dental tools can be used, rather than the dental drill 116, to remove decayed portions of the targeted tooth 106 when creating the prepared cavity area 107.

Still referring to FIG. 2, as previously described, the dental imaging wand 108 can be used to scan portions of the patient's mouth 104 including the targeted tooth 106. In some implementations, portions of the mouth 104 that are proximate to the targeted tooth 106 are also scanned using the dental imaging wand 108. For example, all or a portion of the tooth 112 can be scanned. The dental imaging wand 108 transmits data indicative of the contours and shape of the targeted tooth 106 (and optionally, one or more neighboring teeth 112) to the computer system 110, which is configured to generate a three-dimensional digital image of the targeted tooth 106 or another type of digital impression of the targeted tooth 106. It should be understood from the description herein that devices other than a dental imaging wand 108 can be used to capture imaging data of the targeted tooth 106 and surrounding portions of the mouth 104. For example, Magnetic Resonance Imaging (MRI) technology can be used to capture imaging data for use in generating the three-dimensional digital image of the targeted tooth 106. As another example, fluoroscope or x-ray images taken from several angles can serve as the imaging data used by the computer system 110 to generate the three-dimensional digital image of the targeted tooth 106.

In this embodiment, the computer system 110 receives the digital imaging information from the dental imaging wand 108 and executes a program to generate a CAD model for the customized dental matrix 102. For example, the computer system 110 can include a user interface (e.g., touchscreen, display, keyboard, mouse, etc.), computer-readable memory for storing the digital imaging information, and one or more processors that are configured to execute a software program stored in the computer-readable memory specifically configured to generate the CAD model for the customized dental matrix 102. In some implementations, the computer system 110 first generates a three-dimensional digital image of the targeted tooth 106 and then uses the generated three-dimensional digital image of the targeted tooth 106 to generate the CAD model. In some implementations, the computer system 110 generates the CAD model without first creating a three-dimensional digital image of the targeted tooth 106. The computer system 110 generates the CAD model to define the customized dental matrix 102 to have patient specific, custom-shaped surfaces based on the contours of the targeted tooth 106 and, in some cases, surrounding areas of the mouth 104, such as the tooth 112. The customized dental matrix 102 is fabricated in the customized shape to provide a specific fit around the targeted tooth 106 to preserve spacing between the targeted tooth 106 and surrounding areas of the mouth, to define at least a portion of the periphery of the final shape of filling material applied to the targeted tooth 106, and to reduce the likelihood of seepage of the filling material from the prepared cavity area 107 of the targeted tooth 106 and onto surrounding areas of the gums and mouth 104.

The computer system 110 can include a desktop or portable computer or a custom computer system that is configured to interact with the dental scanning wand 108 and the three-dimensional printer 114. The computer system 110 can use the generated CAD model of the customized dental matrix 102 to transmit instructions to the three-dimensional printer 114 to allow the three-dimensional printer 114 to create the patient-specific, customized dental matrix 102. In some implementations, the computer system 110 creates digital cross-sections of the CAD model and transmits the digital cross-sections to the three-dimensional printer 114. The three-dimensional printer 114 uses the digital cross-sections as guides for "printing" successive layers of the customized dental matrix 102. In some implementations, the computer system 110 transmits a file that includes the CAD model to the three-dimensional printer 114 and the digital cross-sectioning of the CAD model is performed by the three-dimensional printer 114.

In some embodiments, the material used by the three-dimensional printer 114 to create the customized dental matrix 102 comprises a polymer material. Examples of three-dimensional printing materials that can be used by the three-dimensional printer 114 include polypropylene, high-density polyethylene, polystyrene, poly methyl methacrylate, polycarbonates, acrylonitrile butadiene styrene, high-impact polystyrene, styrene-based thermoplastic elastomers, or ethylene propylenediene monomer rubber. In some implementations, the three-dimensional printer 114 can use a multipurpose, non-toxic, transparent photopolymer to create the customized dental matrix 102 so that the customized dental matrix 102 is transparent as described above (i.e., sufficiently transparent so as to permit passage of a UV curing light through the body of the dental matrix 102 and toward the targeted tooth 106).

Figure 3:
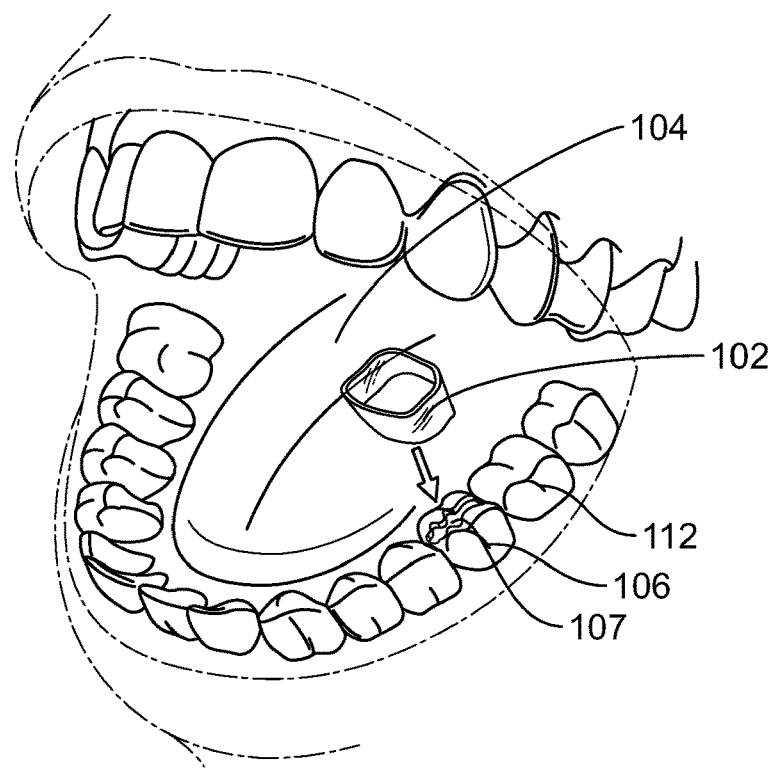
FIG. 3 shows a perspective view of the customized dental matrix of FIG. 2 being inserted over a targeted tooth, in accordance with some embodiments.

Referring now to FIG. 3, after the three-dimensional printer 114 fabricates the customized dental matrix 102 according to the patient-specific imaging data, the matrix 102 can inserted over the targeted tooth 106 so that the inner surfaces of the customized dental matrix 102 form a contoured fit with the surfaces of the targeted tooth 106. In some implementations, the customized dental matrix 102 is created using a flexible polymer material to allow the customized dental matrix 102 to be readily inserted over the targeted tooth 106 (and possibly elastically expanded during the insertion procedure before reaching a snug fit with the contours of the targeted tooth 106). As described above, the inner surfaces of the dental matrix 102 can be customized to take on a shape that closely or exactly matches the outer surfaces of the targeted tooth 106 to provide an improved embrasure form that defines satisfactory contact points between the targeted tooth 106 and its neighboring teeth 112. For example, the dental matrix 102 may have an upper opening and a lower opening in communication with an aperture of the matrix 102, and the lower opening can be noticeably smaller than the upper opening so as to match the small circumference of the targeted tooth at the lower cervical portion of the tooth 106 as compared to the larger circumference at the upper occlusal portion of the tooth 106. Because the dental matrix 102 can be formed of a flexible polymer material, the material at the lower opening may elastically flex during the insertion procedure while passing over the upper occlusal portion of the tooth 106 before seating at the lower cervical portion of the tooth 106 in a snug fit. The custom shape of the dental matrix 102 can additionally allow a practitioner to secure the dental matrix 102 to the targeted tooth 106 without the use of external clamp devices since the dental matrix 102 forms a custom fit with the targeted tooth 106 that includes gripping surfaces of the targeted tooth 106, including the lower cervical portion of the targeted tooth 106.

In some implementations, portions of the outer surfaces of the customized dental matrix 102 are shaped to conform to the contours of neighboring teeth 112. For example, portions of the outer surfaces of the customized dental matrix 102 can be shaped to match the contours of surfaces of the tooth 112 proximate to the targeted tooth 106. Such contoured shaping of the outer surfaces of the customized dental matrix 102 can improve the embrasure between teeth (e.g., the teeth 106 and 112) and define proper distances between newly added filling material applied to the targeted tooth 106 and the tooth 112. The customized dental matrix 102 can be positioned around the targeted tooth 106 so as to at least partially define the periphery of the space for the filling material that is subsequently inserted into the prepared cavity area 107.

In some optional implementations, after the customized dental matrix 102 has been inserted into the mouth 104 to surround the targeted tooth 106, an etching solution can be applied to the prepared cavity area 107. The etching solution can be applied to remove a smear layer within the prepared cavity area 107 or any debris within the prepared cavity area 107 that has been left after decayed portions of the targeted tooth 106 have been removed to create the prepared cavity area 107. The etching solution can also serve to open pores in the dentin of the targeted tooth 106 to facilitate improved cohesion of bonding fluid with the prepared cavity area 107 of the targeted tooth 106. After etching liquid is applied, the prepared cavity area 107 can be dried (e.g. through application of pressurized air) to prepare the prepared cavity area 107 for application of bonding fluid.

Also in some optional implementations, after application and removal of the etching solution, a layer of adhesive material or bonding fluid can be applied to the prepared cavity area 107. The customized dental matrix 102 can at least partially define an area for application of the bonding fluid. The customized dental matrix 102 can contain the bonding fluid to minimize contact between the bonding fluid and portions of the targeted tooth 106 that do not need to be reconstructed using composite resin. The customized shape of the dental matrix 102 reduces the likelihood of the bonding fluid leaking onto the gums and surrounding areas of the mouth 104 during application. In some implementations, the bonding fluid is applied to the prepared cavity area 107 in a relatively thin coat. After application of the bonding fluid, a dental curing light can be used to cure the bonding fluid by applying ultraviolet (UV) light to the bonding fluid. This curing process is used to harden the bonding fluid.

Figure 4:
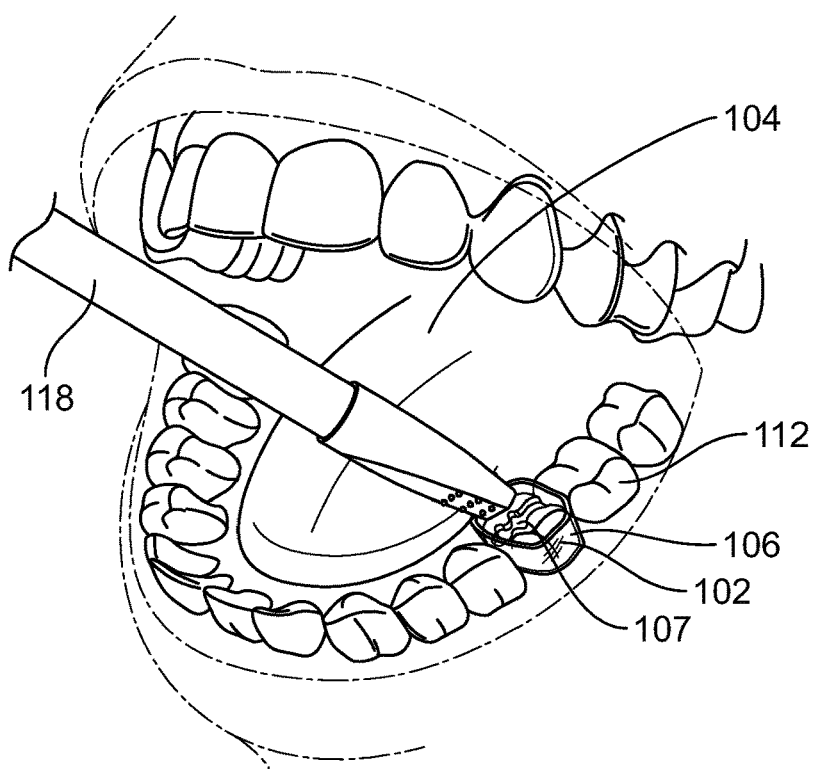
FIG. 4 shows a perspective view of the customized dental matrix of FIG. 3 fitted onto the targeted tooth during a dental procedure.

Referring now to FIG. 4, after the dental matrix 102 has been inserted to surround the targeted tooth 106 (and, preferably, after application of the etching solution and bonding fluid as described above), the practitioner can use an applicator tool 118 to apply a filling material to the prepared cavity area 107. For example, the applicator tool 118 can include a composite resin applicator tool that is configured to apply a composite resin to the prepared cavity area 107. In some implementations, filling material other than composite resin can be applied to the prepared cavity area 107 to restore the targeted tooth 106. For example, gold, porcelain, or silver amalgam can be used as filling material. In some implementations, the composite resin can be applied to the prepared cavity area 107 in layers, with each layer of the applied composite resin being cured using UV light prior to application of a subsequent composite resin layer. For example, referring to FIG. 5A, after application of a first layer of composite resin, a curing light tool 122 can be used to apply UV light to the layer of composite resin to cure the composite resin. Then, referring again to FIG. 4, after curing of the first layer of composite resin, a subsequent layer of composite resin is applied to the prepared cavity area 107. The subsequent layer of composite resin is then cured using the curing light tool 122. Additional iterations of applying layers of composite resin and curing the applied layers of composite resin can be performed as necessary to restore the targeted tooth 106.

The customized dental matrix 102 can at least partially define a peripheral wall for application of composite resin throughout the process of applying and curing layers of composite resin. The customized dental matrix 102 can contain the composite resin to minimize contact between the composite resin and portions of the targeted tooth 106 outside of the prepared cavity area 107. The customized shape of the dental matrix 102 reduces the likelihood of the composite resin leaking onto the gums and surrounding areas of the mouth 104 during application. The customized dental matrix 102 can also define proper spacing between composite resin applied to the targeted tooth 106 and surrounding teeth 112.

Figure 5A:
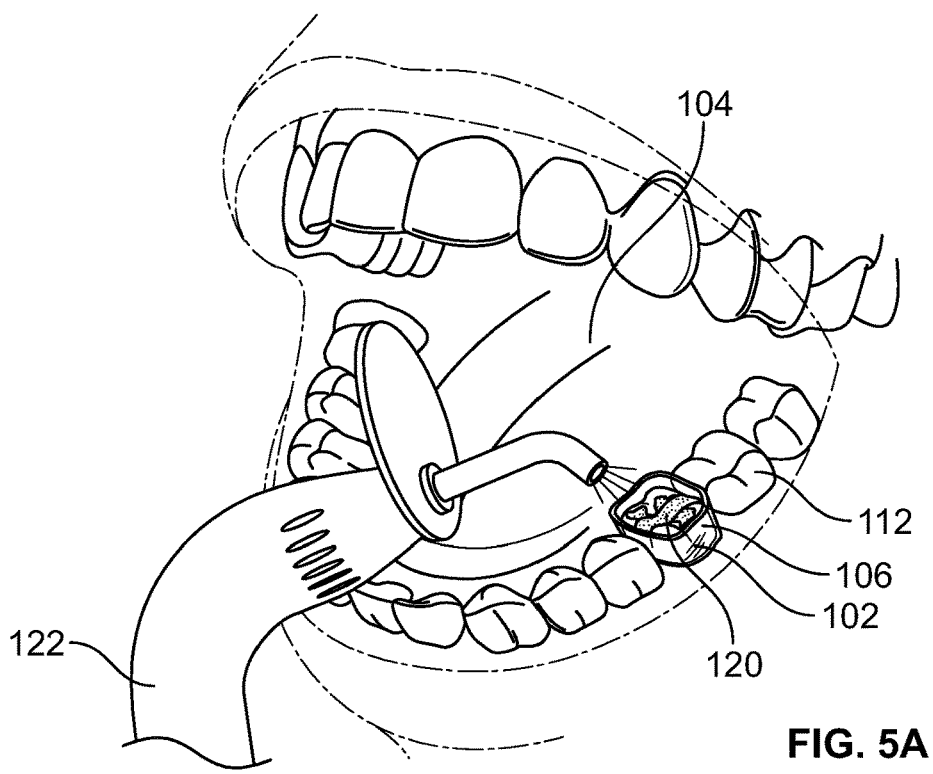
FIG. 5A shows a perspective view of the customized dental matrix of FIG. 3 in use during a curing step of the dental procedure.
Figure 5B:
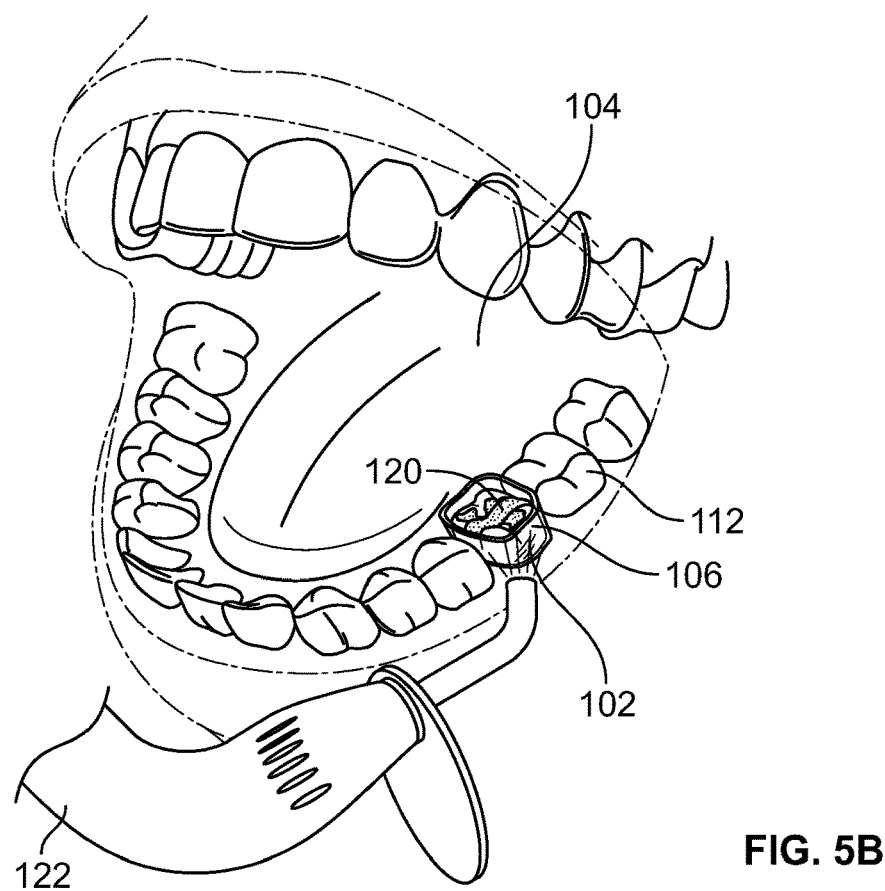
FIG. 5B shows another perspective view of the customized dental matrix of FIG. 3 in use during a curing step of the dental procedure.

Referring now to FIGS. 5A-B, in some implementations of the system, a practitioner can use the curing light tool 122 to direct UV light to filling material 120 (e.g., composite resin) that has been applied to the prepared cavity area 107 of the targeted tooth 106. In the example shown, the customized dental matrix 102 is constructed from a transparent material (as described above). This allows the filling material 120 to be cured even if the filling material 120 is deposited in a region that is not accessible or otherwise difficult to access from the uppermost face of the tooth 106. Also, this capability to transmit the UV light through the dental matrix 102 allows each layer of filling material 120 to be cured without the customized dental matrix having to be removed 102 between each filling material layer application phase of the filling process. As shown in FIGS. 5A-B, in this particular embodiment, the transparent nature of the customized dental matrix 102 allows UV light to be applied to the filling material 120 from multiple angles that might not otherwise be available when using some traditional matrix devices. For example, as shown in FIG. 5B, the curing light tool 122 can be positioned to emit UV light through a side of the customized dental matrix 102 onto the filling material 120. Allowing for the application of UV light through the customized dental matrix 102 during a curing phase is particularly beneficial when filling material has been applied to cervical-third or middle-third of the targeted tooth 106.

After curing of the filling material 120, the customized dental matrix 102 can be removed from the targeted tooth 106. The dental matrix can be configured as a single-use, disposable device that is discarded after the filling material 120 is properly cured in the prepared cavity 107. In some optional implementations, after the customized dental matrix 102 has been removed from the targeted tooth 106, composite resin that has been applied to the targeted tooth 106 can be polished or trimmed to create a desired shape for the restored tooth 106 (e.g., polished or trimmed along the upper-most surface to provide a satisfactory bite). In some implementations, polishing or trimming of the filling material 120 is not necessary since the customized dental matrix 102 defined a custom shape for the filling material 120 to create desired shape for the filling material 120 and ensure desired spacing between the restored tooth 106 and adjacent teeth 112.

Figure 6:
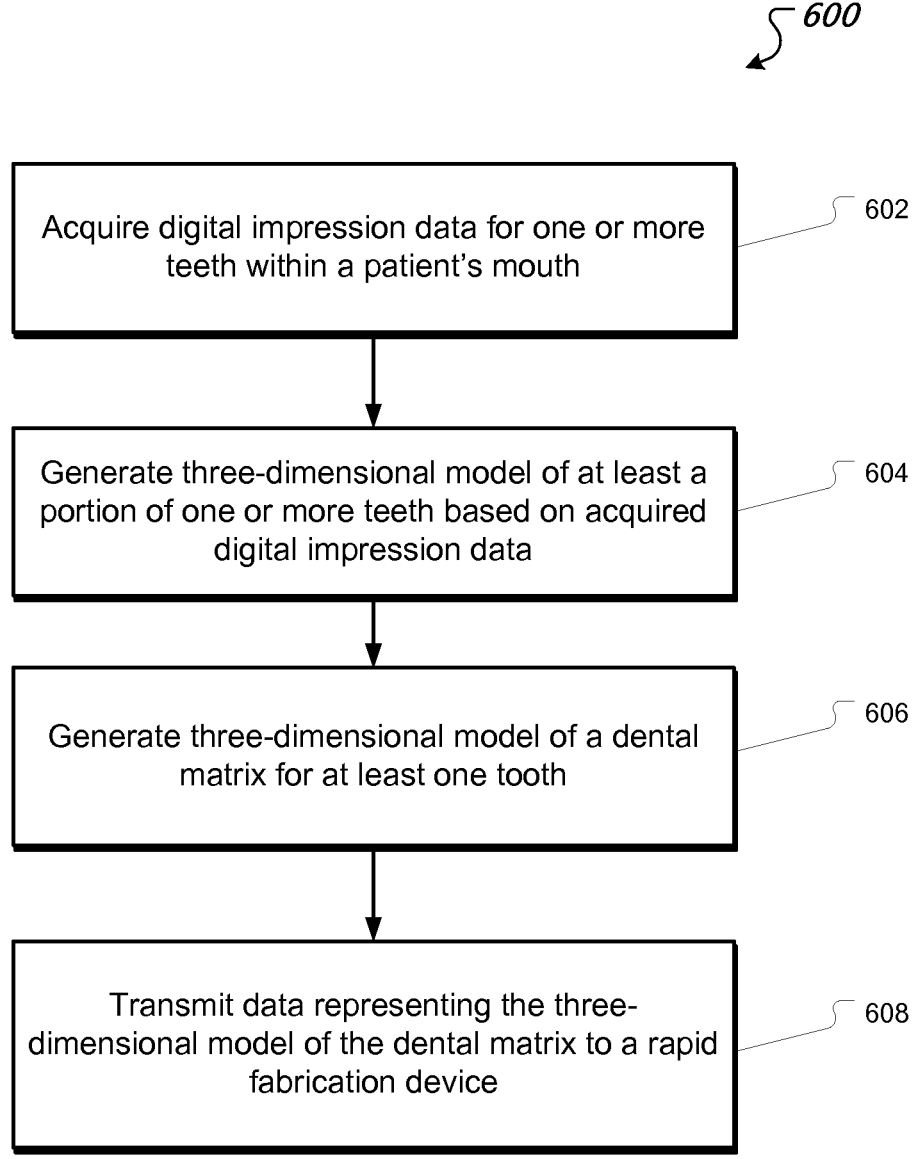
FIG. 6 is a flowchart illustrating an example procedure for making a customized dental matrix.

Referring now to FIG. 6, an example process 600 for making a customized dental matrix includes acquiring digital impression data for one or more teeth within a patient's mouth (602). For example, a practitioner, such as a dentist can use a dental scanning wand (e.g., the dental scanning wand 108 of FIG. 1) to capture digital image impression data for use in generating a digital impression of all or portions of a patient's mouth. In some implementations, the dental scanning wand is used to collect digital impression data for a tooth having a prepared cavity area that requires application of filling material. In some implementations, the dental scanning wand is used to collect digital impression data for multiple teeth within a patient's mouth. A scan of multiple teeth within the patient's mouth can be used, for example, during a process for creating a multi-tooth customized dental matrix, or a customized carrier tray for applying fluoride treatment or whitening treatment to a patient's teeth. In some implementations, devices other than a dental scanning wand can be used to acquire the digital impression data. For example, Magnetic Resonance Imaging (MRI), fluoroscope or x-ray technology can be used to acquire the digital impression data. In some implementations, the digital impression data is acquired from the dental scanning wand (or other imaging device) by a computer system such as the computer system 110 of FIG. 1.

The process 600 further includes generating a three-dimensional model of at least a portion of one or more teeth based on the acquired digital impression data (604). For example, a computer system (e.g., the computer system 110 of FIG. 1) can use the digital impression data acquired at 602 to generate a three-dimensional computer aided design (CAD) model of at least a portion of the patient's mouth. In some implementations, the generated three-dimensional model utilizes only a portion of the acquired digital impression data. In some implementations, such as, for example, during a dental matrix creation process, the three-dimensional model represents only a targeted tooth having a prepared cavity area and surrounding teeth and gums. In some implementations, such as, for example, during a customized fluoride or whitening treatment carrier tray creation process, the three-dimensional model represents all teeth and surrounding mouth areas of a patient's mouth, or all teeth and surrounding gum areas for an upper or lower set of the patient's teeth. The generated three-dimensional model can be stored in a memory of the computer system, and/or transmitted to other computers and electronic devices in communication with the computer system.

The process 600 further includes generating a three-dimensional model of a dental matrix for at least one tooth (606). For example, the computer system can use the three-dimensional model generated at 604 to generate a CAD model for fabricating a customized dental matrix. The computer system can generate the CAD model such that the dental matrix defined by the CAD model is shaped to match contours of one or more teeth of the patient for which digital impression data has been acquired. The computer system can also generate the CAD model such that the dental matrix defined by the CAD model defines satisfactory embrasure forms between teeth of the patient. For example, the CAD model defines a shape for the inner surfaces of the dental matrix such that the inner surfaces of the dental matrix conform to the contours of one or more teeth of the patient when in use during a cavity filling procedure. In some implementations, the CAD model defines portions of the outer surfaces of the dental matrix to engage teeth and gums in close proximity a targeted tooth in a patient-specific, customized manner to define preferred embrasure forms and spacing between adjacent teeth.

In some alternate implementations, the process 600 can include generating a three-dimensional model of a carrier tray (e.g., for applying fluoride or whitening treatment to a patient's teeth) that is customized to fit specific contours of the patient's teeth. Generating a carrier tray that is customized to the shape of the patient's teeth can allow for more efficient, effective, and even coverage of the patient's teeth. For example, use of a customized carrier tray during a fluoride application process can ensure even distribution of fluoride over and among the patient's teeth while, in some cases, reducing the amount of fluoride required for the fluoride treatment.

The process 600 further includes transmitting data representing the three-dimensional model of the dental matrix to a rapid fabrication device (608). For example, the computer system can transmit data representing the three-dimensional model to a three-dimensional printer (e.g., the three-dimensional printer 114 of FIG. 1). The rapid fabrication device can use the transmitted data representing the three-dimensional model to create the dental matrix. After creation of the custom dental matrix, the dental matrix can be inserted over one or more teeth of a patient during a cavity filling procedure.

In some implementations, digital cross-sections of the three-dimensional model are created and transmitted to the rapid fabrication device. For example, a three-dimensional printer can use the digital cross-sections as guides for depositing successive layers of material to create the dental matrix. In some implementations, a file that includes entire three-dimensional model (such as a CAD file) is transmitted to the rapid fabrication device. In some such implementations, digital cross-sectioning of the three-dimensional model is performed by rapid fabrication device. In some implementations, digital cross-sections are not required by the rapid fabrication device to generate the dental matrix.

In some alternate implementations, the process 600 can include generating a customized carrier tray (e.g., for applying fluoride or whitening treatment to a patient's teeth) from a three-dimensional model of the carrier tray. The carrier tray is customized to fit specific contours of the patient's teeth. The three-dimensional model of the customized carrier tray can be transmitted from the computer system to a rapid fabrication machine (e.g., a three-dimensional printer) to allow the rapid fabrication machine to create the customized carrier tray. In some implementations, this can include transmission of digital cross-sections of the three-dimensional model as described above.

Figure 7:
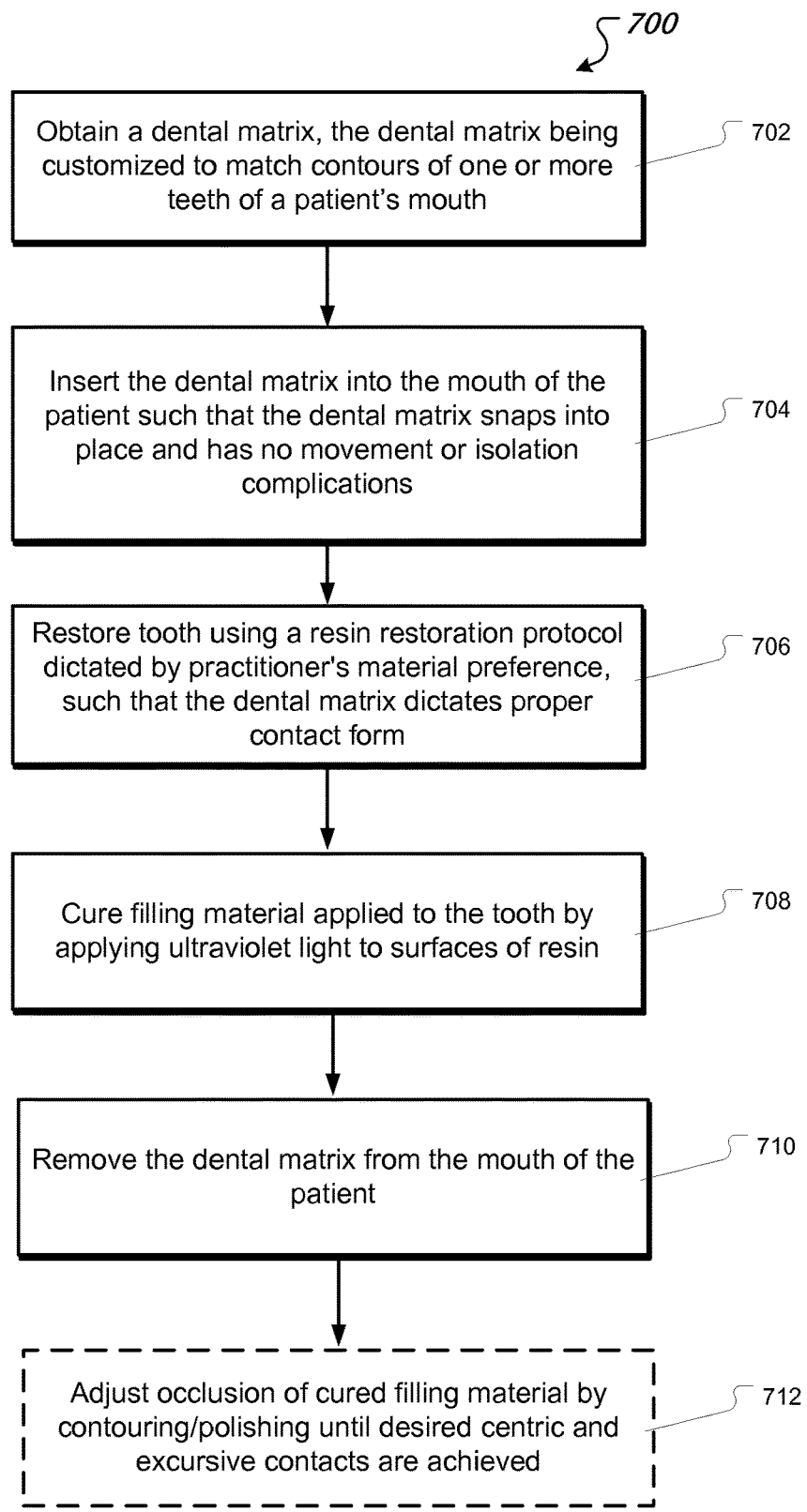
FIG. 7 is a flowchart illustrating an example procedure for using a customized dental matrix during a dental filling procedure.

Referring now to FIG. 7, an example process 700 for using a customized dental matrix during a dental filling procedure includes obtaining a dental matrix, the dental matrix being customized to match contours of one or more teeth of a patient's mouth (702). For example, a practitioner (e.g., a dentist) can obtain a customized dental matrix by obtaining digital impression data for the one or more teeth (e.g., using a digital imaging wand), using a computer system to generate a three-dimensional model of the customized dental matrix, and "printing" the customized dental matrix using a three-dimensional printer. In some implementations, this process can be performed on the premises during a single office visit for the patient. As another example, digital impression data for the one or more teeth can be acquired and transmitted to a remote computing system to allow the customized dental matrix to be manufactured at a specialized facility. The customized dental matrix can then be delivered to the dentist's office (e.g., by an express courier delivery service or the like) for use during a dental filling procedure. In some implementations, the dental matrix is a multi-tooth dental matrix configured to encompass two or more teeth when inserted into the patient's mouth. A multi-tooth dental matrix can be used, for example, during a cavity filling procedure in which decayed portions of multiple teeth require repair through the application of filling material (e.g., composite resin).

The process 700 further includes inserting the dental matrix into the mouth of the patient such that the dental matrix snaps into place and has no movement or isolation complications (704). For example, referring to FIGS. 3 and 4, the customized dental matrix 102 is inserted over the targeted tooth 106 to form a custom fit with the contours of the targeted tooth 106. In some implementations, the dental matrix is created from a flexible material to allow for easier insertion of the dental matrix over the corresponding tooth. The customized internal shape of the dental matrix obviates the need for external clamps to hold the dental matrix into place. Due to the customized fit of the dental matrix and its flexible properties, it can form a seal with a lower cervical rim of the corresponding tooth to thereby reduce the likelihood of filling material leaking onto the gums and surrounding areas of the mouth during deposition of the filling material. In some implementations, the dental matrix is a multi-tooth dental matrix and is inserted over multiple teeth within the patient's mouth.

The process 700 further includes restoring a tooth using a resin restoration protocol dictated by the practitioner's material preference, such that the dental matrix dictates proper contact form (706). For example, an etching solution can be applied to a prepared cavity area of the tooth to remove a smear layer and/or debris left over from a drilling procedure. The etching solution can also serve to open pores in the dentin of the tooth to allow for better adhesion of a bonding layer. The practitioner can then, for example, apply bonding fluid to the prepared cavity area, apply UV light to the bonding fluid to cure the bonding fluid, and then apply a layer of composite resin. The dental matrix can at least partially define an area in which composite resin is applied in order to provide an improved embrasure form that defines satisfactory contact points between the tooth on which the resin restoration protocol is being performed, and one or more adjacent teeth.

The process 700 further includes curing the filling material (e.g., composite resin) applied to the tooth by applying ultraviolet light to surfaces of the resin (708). For example, referring to FIG. 5A, the curing light tool 122 is used to apply UV light to the filling material 120 to harden the filling material 120. In some implementations, the customized dental matrix is created from a transparent material to allow UV light to be imparted on the composite resin through the dental matrix. For example, referring to FIG. 5B, the curing light tool 122 can shine UV light through the customized dental matrix 102 to cure the filling material 120. Constructing the dental matrix from a transparent material allows successive layers of composite resin to be applied and cured without requiring removal of the dental matrix between each composite resin application step. In some implementations, several iterations of applying composite resin and curing the applied layer can be repeated to restore a tooth.

The process 700 further includes removing the dental matrix from the mouth of the patient (710). In some implementations, the dental matrix is created using a flexible or semi-flexible material to allow the dental matrix to be readily removed with minimal effort.

The process 700 optionally includes adjusting occlusion of cured filling material by contouring/polishing until desired centric and excursive contacts are achieved (712). For example, the practitioner can contour the filling material using a drill in order to achieve a desired shape for the tooth such that centric and excursive contacts between the tooth and adjacent teeth are adequate. As another example, the practitioner can smooth the newly applied filling material using a prophy cup along with an abrasive polishing compound. In some implementations, the filling material does not require contouring and/or polishing since the customized dental matrix has least partially defined a shape for the filling material in order to provide an improved embrasure form that defines satisfactory contact points between the tooth on which the resin restoration protocol is being performed, and one or more adjacent teeth.

Figure 8:
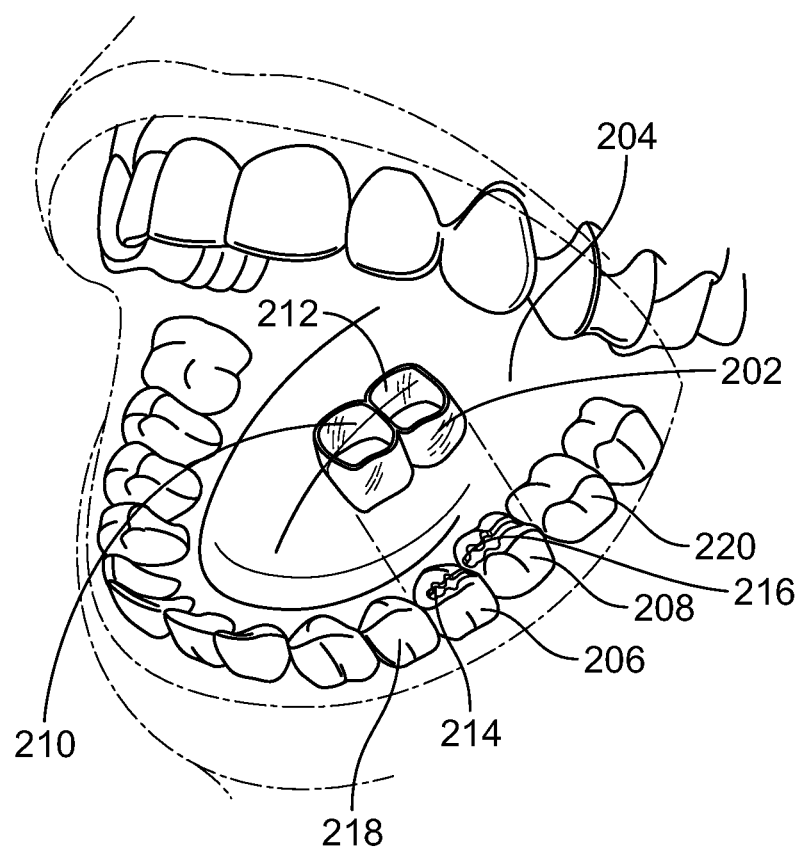
FIG. 8 shows a perspective view of a customized multi-tooth dental matrix for use during a dental procedure.

Referring now to FIG. 8, a dental matrix fabrication system, such as the system 100 of FIG. 1, can be used to create a customized multi-tooth matrix 202 for insertion into a patient's mouth 204 during a dental filling procedure. For example, a dental imaging wand can be used to obtain digital impression data for teeth 206 and 208 of the mouth 204, and optionally other surrounding areas of the mouth 204. The digital impression data can be transmitted to a computer system (e.g., system 110 as shown in FIG. 1) for generation of a three-dimensional model of the customized multi-tooth matrix 202 configured to conform to the contours of the teeth 206 and 208. The three-dimensional model can then be used by a rapid fabrication machine (such as the three-dimensional printer 114 as shown in FIG. 1) to create the customized multi-tooth matrix 202.

In the example shown, the customized multi-tooth matrix 202 includes a first aperture 210 for engaging the tooth 206 and a second aperture 212 for engaging the tooth 208, with an optional separator wall formed therebetween. The customized multi-tooth matrix 202 can be designed and fabricated such that the inner surfaces of the aperture 210 conform to the contours of the tooth 206 when the customized multi-tooth matrix 202 is inserted over the teeth 206 and 208. Similarly, the customized multi-tooth matrix 202 can be designed and fabricated such that the inner surfaces of the aperture 212 conform to the contours of the tooth 208 when the customized multi-tooth matrix 202 is inserted over the teeth 206 and 208.

The customized multi-tooth matrix 202 can be inserted over the teeth 206 and 208 to at least partially define shapes for filling material applied to a prepared cavity area 214 of the tooth 206 and a prepared cavity area 216 of the tooth 208. The customized multi-tooth matrix 202 is designed to match the contours of the teeth 206 and 208 and surrounding areas of the mouth 204 to define preferred embrasure forms between the teeth 206 and 208 and to provide proper spacing between the tooth 206 and the tooth 208 is maintained when filling material is deposited to the prepared cavity areas 214 and 216. For example, the optional separator wall formed between the first and second apertures 206 and 212 can be wider at the lower end of the matrix 202 than at the upper end of the matrix 202 so as to properly defined the selected cervical or gingival embrasure (fit with the lower end of the separator wall) and the selected occlusal embrasure (fit with the upper end of the separator wall). In some implementations, outer surfaces of the customized multi-tooth matrix 202 can be shaped to match contours of portions of the surfaces of adjacent teeth 218 and 220 to define preferred embrasure forms and spacing between teeth 206 and 218 and between teeth 208 and 220.

As filling material is applied to the prepared cavity areas 214 and 216, the customized multi-tooth matrix 202 causes the filling material to take on the selected anatomical shape for the teeth 206 and 208 since the inner surfaces of apertures 210 and 212 have been specifically tailored to conform to the selected shape that matches contours of the teeth 206 and 208 respectively (including the contours of the cervical-third of each tooth). In some implementations, the customized multi-tooth matrix 202 is manufactured from a flexible material. The customized fit of the multi-tooth matrix 202 in combination with flexible properties allow the customized multi-tooth matrix 202 to form a seal with a lower cervical rim of each of the teeth 206 and 208 to thereby reduce the likelihood of bonding fluid or filling material leaking onto the gums and surrounding areas of the mouth 204 during a direct resin restoration procedure or the like.

In some implementations, the customized multi-tooth matrix 202 can comprise a transparent material (i.e., sufficiently transparent so as to permit passage of a UV curing light through the body of the customized multi-tooth matrix 202 and toward the teeth 206 and 208). The customized multi-tooth matrix 202 can be formed as a transparent or semi-transparent structure for purposes of permitting UV rays from a dental curing light to transmit through the customized multi-tooth matrix 202 to cure filling material applied to the prepared cavity areas 214 and 216 during a curing process of a direct resin restoration procedure or the like.

Figure 9A:
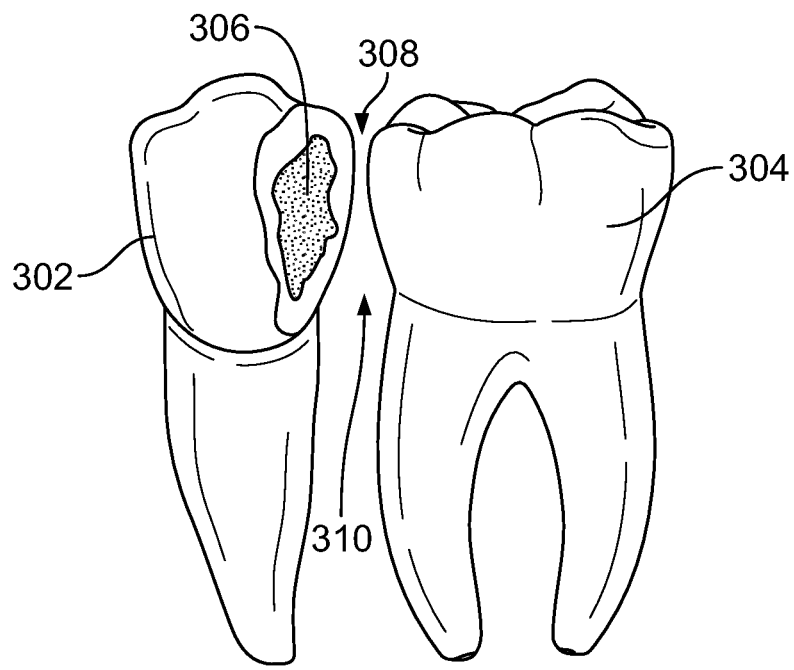
FIG. 9A shows a side view of a tooth having a prepared cavity for receiving a filling material in relation to an adjacent healthy tooth.
Figure 9B:
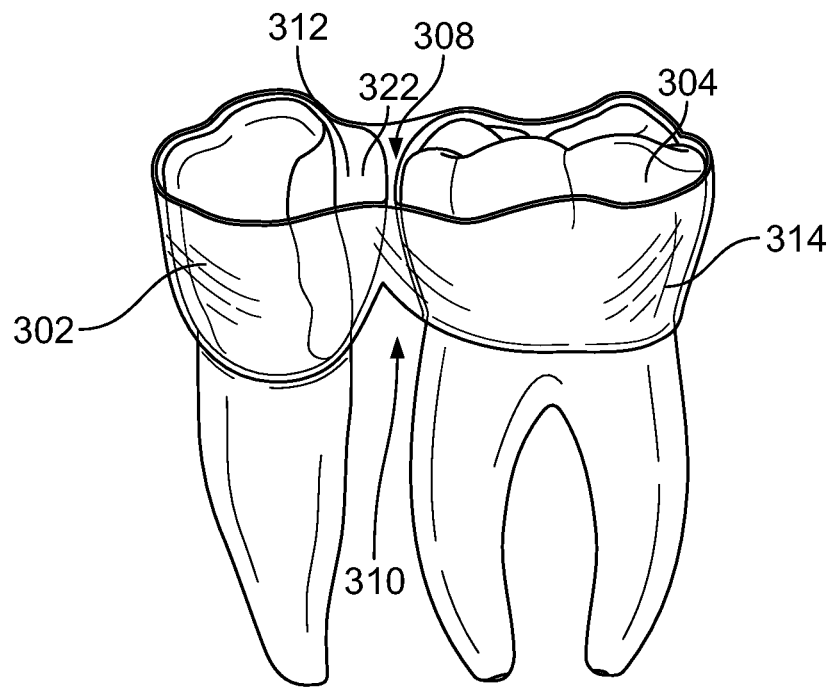
FIG. 9B shows a side view of a customized dental matrix inserted over portions of the teeth of FIG. 9A.
Figure 10A:
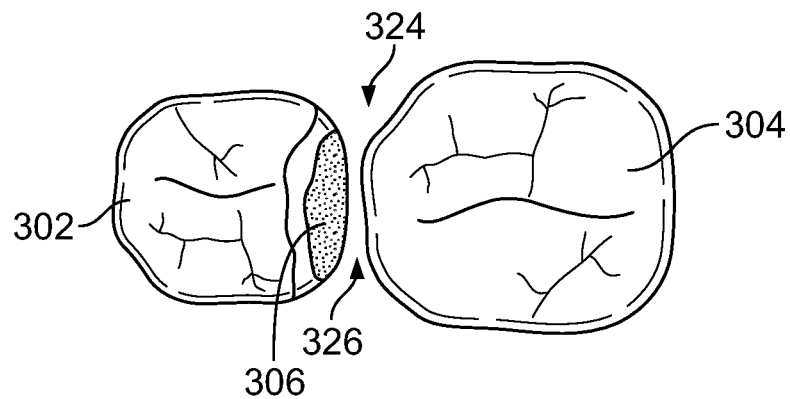
FIG. 10A shows a top view of the teeth of FIG. 9A.
Figure 10B:
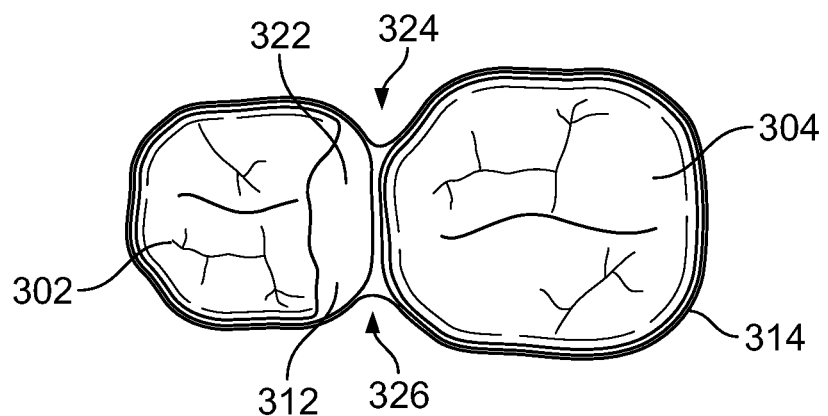
FIG. 10B shows a top view of the customized dental matrix of FIG. 9B inserted over portions of teeth of FIG. 9A.

Referring now to FIGS. 9A-B and 10A-B, the system or processes described above can be implemented to provide a customized dental matrix 314 so as to treat a tooth having a decay region 306 extending to (or beyond) the middle-third of a tooth 302. FIGS. 9A-B shows a side or lingual view of two adjacent teeth 302 and 304 located within a patient's mouth, while FIGS. 10A-B shows the same teeth 302 and 304 in a top down or occlusal view.

Referring now to FIGS. 9A and 10A, the tooth 302 is suffering from a dental caries at a decayed region 306 on a side adjacent to the tooth 304. FIG. 9 shows the relational spacing of the teeth 302 and 304 prior to a direct resin restoration procedure, including an occlusal embrasure 308 between the teeth 302 and 304 and a cervical (or gingival) embrasure 310 between the teeth 302 and 304. The aforementioned system 100 can be employed to treat the tooth 302 and maintain proper occlusal and cervical embrasure at the end of a direct resin restoration procedure. For example, the system 100 (FIG. 1) can be used to fabricate a dental matrix 314 (FIGS. 9B and 10B) that defines a selected occlusal embrasure 308 and a selected cervical embrasure 310 for purposes of hindering food from becoming lodged between the teeth 302 and 304 and to stabilize a dental arch of the patient by assuring consistent anchorage of teeth within the patient's mouth. Also, the dental matrix 314 can define the selected occlusal embrasure 308 and the selected cervical embrasure 310 to preserving proper contact points between the teeth 302 and 304 for purposes of reducing the likelihood of "drifting" of teeth within the patient's mouth. Similarly, as shown in FIGS. 10A and 10B, the system 100 can be used to fabricate the dental matrix 314 to define a selected buccal embrasure 324 and a selected lingual embrasure 326 between the teeth 302 and 304. Having proper buccal and lingual embrasures between the teeth 302 and 304 can also hinder food from becoming lodged between the teeth 302 and 304. In some implementations, the buccal and lingual embrasures as defined by the dental matrix 314 provide an adequate breadth of the proximal contact between the teeth 302 and 304 to minimize lodging of food between the teeth 302 and 304. Accordingly, the dental matrix 102 can be tailored to each patient's specific anatomical features of the targeted tooth 106 and its neighboring teeth, and furthermore, the dental matrix 102 can be promptly fabricated (while the patent is waiting the dental facility) according to the specific anatomical shape and size of that particular patient.

Referring to FIGS. 9B and 10B, the decay region 306 has been removed or otherwise treated on the tooth 302 (e.g., using a dental drill) to create a prepared cavity area 312. The customized dental matrix 314 (e.g., fabricated using the system 100 or other process as described above) can be configured to match the contours of the teeth 302 and 304. It should be understood from the description herein that the customized dental matrix 314 can be fabricated as a single-tooth matrix, which may include a single aperture to fit with the tooth 302 and which does not wrap around the second tooth 304. In the example shown, the customized dental matrix 314 comprises a transparent, flexible material to allow the dental matrix 314 to conform to the shapes of the teeth 302 and 304 and to allow UV light to be transmitted through the dental matrix 314 during a curing process. Due to the customized fit of the dental matrix 314 and its flexible properties, it can form a seal with a lower cervical rim of one or both of the teeth 302 and 304 to thereby reduce the likelihood of filling material leaking onto the gums and surrounding areas of the a mouth that contains the teeth 302 and 304 during the deposition of the filling material. Accordingly, FIG. 9B shows that the dental matrix 314 can define the selected occlusal embrasure 308 and the selected cervical embrasure 310, while FIG. 10B shows that the dental matrix 314 can define the selected buccal embrasure 324 and the selected lingual embrasure 326 between the teeth 302 and 304.

Figure 11:
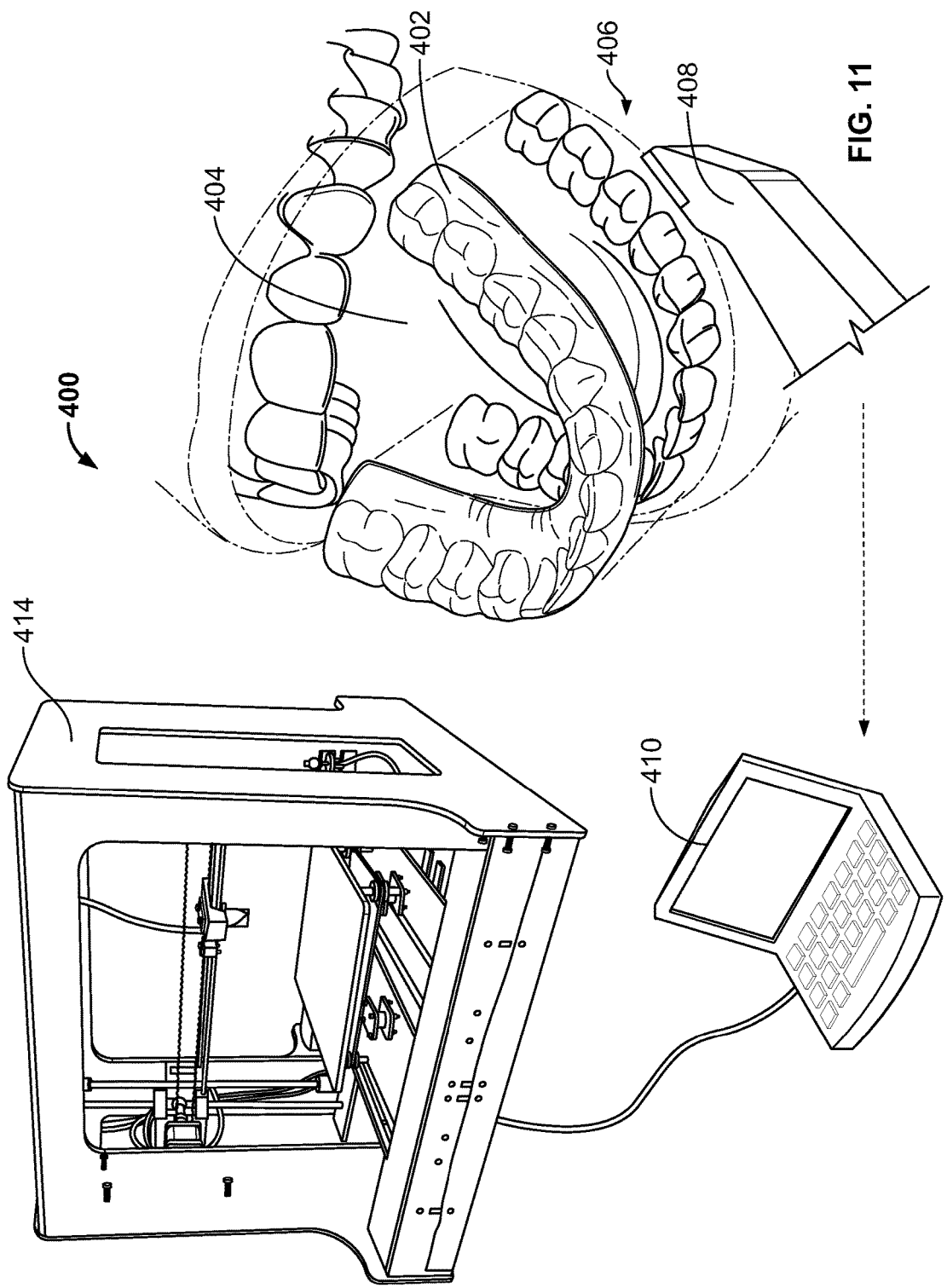
FIG. 11 shows a perspective view of a customized teeth tray for use during a dental procedure.

Referring to FIG. 11, some embodiments of a system 400 for applying fluoride treatment, whitening treatment, or other dental treatments can employ a customized carrier tray 402 fit the patient-specific contours of a particular set of teeth 406. For example, the customized carrier tray 402 can be fabricated to form a custom fit with the teeth 406 along the lower jaw of a mouth 404 (and a similar carrier tray for the teeth along the upper jaw can likewise be fabricated using the system 400). In some implementations, the carrier tray 402 can be created onsite and in response to receiving digital images or another type of digital impression of the patient's teeth 406 (e.g., using a dental imaging wand 408 and a computer system 410). For example, the carrier tray 402 can be formed in an intra-office process (e.g., in a dentist's facility using a rapid fabrication machine 414 such as a three-dimensional printer apparatus or the like) for use in applying fluoride, whitening gel, or other dental treatments to the teeth 406. In such embodiments, the carrier tray 402 is not necessarily a prefabricated, one size fits all tray that is located in the inventory of the dentist's facility before the patient arrives, but instead the carrier tray 402 can be promptly fabricated according to the specific anatomical shape and size of the patient's mouth 404 and teeth 406 while that patient is waiting in the dental chair or in another area of the same dentist's facility. The customized carrier tray 402 can be implemented in a manner that adds efficiencies to the dental procedures (e.g., a whitening gel application procedure or another procedure), that reduces the likelihood of excessive pressure on non-anesthetized gingival tissues, and that provides an improved fitting to for the teeth 406.

Briefly, in use, the customized carrier tray 402 can be inserted into a mouth 404 of a patient during a dental procedure, such as a fluoride application procedure, a whitening gel application procedure, or the like. In the depicted embodiments, the customized carrier tray 402 is preferably inserted into the mouth 404 such that the customized carrier tray 402 fits over the teeth 406 of the patient. For example, whitening gel can be distributed within the customized carrier tray 402. The customized carrier tray 402 can then be inserted over the teeth 406 to evenly apply the whitening gel to the teeth 406. The carrier tray 402 can be customized to fit specific contours of the targeted teeth 406 to more efficiently and evenly distribute fluoride, whitening gel, or another dental application across and among the teeth 406.

The customized carrier tray 402 can be fabricated using a process similar to those described above for fabricating customized dental matrices. For example, a process for fabricating the customized carrier tray 402 can closely resemble the processes described above with reference to FIG. 1 for fabricating the customized dental matrix 102. In some implementations, a process for fabricating the customized carrier tray 402 can include acquiring digital imaging data for the teeth 406 and areas of the mouth 404 surrounding the teeth 406 using the digital imaging wand 408. The digital imaging data can then be transferred to the computer system 410 for use in generating a three-dimensional model of the teeth 406 and portions of the mouth 404. The computer system 410 can be, for example, a personal computer, a specialized computer system, or a network of computers coupled with Computer Aided Design (CAD) software for generating three-dimensional models. The computer system 410 can use a generated three-dimensional model of the teeth 406 and portions of the mouth 404 to generate a three-dimensional model (e.g., a CAD model) of the customized carrier tray 402.

The computer system 410 can then transfer data indicative of the three-dimensional model of the customized carrier tray 402 to the rapid fabrication machine 414 (e.g., a three-dimensional printer). In some implementations, information provided to the rapid fabrication machine 414 can include digital cross-sections of the CAD model created by the computer system 410. The rapid fabrication machine 414 uses the digital cross-sections as guides for "printing" successive layers of the customized carrier tray 402. In some implementations, the computer system 410 transmits a file that includes the CAD model to the rapid fabrication machine 414 and the digital cross-sectioning of the CAD model is performed by the rapid fabrication machine 414.

In some implementations, digital impression data for the teeth 406 and portions of the mouth 404 are acquired and the customized carrier tray 402 is fabricated on-site in a practitioner's office during a single office visit. After the customized carrier tray 402 has been created, the customized carrier tray 402 can be used to apply fluoride, whitening gel, or other dental applications to the teeth 406.

A number of embodiments of the invention have been described. Nevertheless, it will be understood that various modifications may be made without departing from the spirit and scope of the invention. Accordingly, other embodiments are within the scope of the following claims.

What is claimed is:

1. A method for using a dental matrix with a targeted tooth, the method comprising:

scanning a targeted tooth of a patient using a digital imaging dental tool to generate digital impression data of at least the targeted tooth, wherein the targeted tooth has been predetermined for a tooth preparation procedure in which a portion of the targeted tooth is removed;

after scanning the targeted tooth, preparing the targeted tooth of the patient in a dental facility building for receiving a filling material by removing decayed portions of the targeted tooth;

after preparing the targeted tooth for receiving the filling material, fabricating at a rapid fabrication device in the dental facility building a patient-specific dental matrix for insertion along the targeted tooth of the patient, the patient-specific dental matrix being fabricated based at least in part on the digital impression data for the targeted tooth of the patient collected prior to removal of the decayed portions of the targeted tooth, the dental matrix having an inner surface that defines a shape for filling material to be applied to the targeted tooth during a dental filling procedure;

inserting the patient-specific dental matrix along the targeted tooth of the patient in the dental facility building such that the dental matrix surrounds the targeted tooth on four sides, including the buccal and lingual sides; and performing the dental filling procedure by applying filling material to the targeted tooth such that a portion of the inner surface of the dental matrix retains the filling material and defines a shape of the filling material.

2. The method of claim 1, wherein the patient-specific dental matrix comprises a transparent polymer material, and the patient-specific dental matrix includes an aperture defined by a curved wall surface of the dental matrix, wherein the curved wall surface is shaped to correspond to one or more contours of a corresponding surface of the targeted tooth;

wherein the transparent polymer material is configured to transmit ultraviolet light through the curved wall of the matrix to allow for curing of filling material applied to the targeted tooth and located within the aperture opening of the dental matrix to be cured by the ultraviolet light transmitted through the dental matrix.

3. The method of claim 2, wherein the aperture of the patient-specific dental matrix has a lower opening at a lower end of the curved wall surface and an upper opening at an upper end of the curved wall surface, the lower opening being smaller than the upper opening, and wherein the curved, wall is flexible such that the lower opening of the aperture is configured to elastically deform during said inserting over an occlusal portion of the targeted tooth having a larger circumference than the lower opening of the aperture.

4. The method of claim 2, wherein the digital impression data for the targeted tooth is obtained via the, digital dental imaging tool in the dental facility building and stored at a computer system in the dental facility building.

5. The method of claim 1, wherein the digital impression data for the targeted tooth is obtained via the digital dental imaging tool in the dental facility building and stored at a computer system in the dental facility building.

6. The method of claim 1, further comprising:
curing the filling material applied to the targeted tooth by transmitting a dental curing light through at a least a portion of the patient-specific dental matrix.

7. The method of claim 6, further comprising:
removing the patient-specific dental matrix from the targeted tooth after curing of the filling material.

8. The method of claim 1, wherein the patient-specific dental matrix comprises a flexible, biocompatible, polymer material.

9. The method of claim 1, wherein the patient-specific dental matrix comprises polypropylene.

10. The method of claim 1, wherein the patient-specific dental matrix comprises high-density polyethylene.

11. The method of claim 1, wherein the patient-specific dental matrix comprises polystyrene.

12. The method of claim 1, wherein the patient-specific dental matrix comprises a styrene-based thermoplastic elastomer.

13. The method of claim 1, further comprising generating, at a computer system in communication with the rapid fabrication device, a three-dimensional model of the patient-specific dental matrix prior to fabricating the patient-specific dental matrix.

14. The method of claim 13, wherein a shape of the patient-specific dental matrix is defined by the three-dimensional model and corresponds to a shape of the outer surface of the targeted tooth prior to the targeted tooth being prepared for receiving the filling material.

15. The method of claim 1, wherein the rapid fabrication device comprises a three-dimensional printer configured to create the dental matrix through deposition of multiple layers of fabrication material.

16. The method of claim 1, wherein the patient-specific dental matrix comprises a transparent material that allows ultraviolet light to transmit entirely through at least a portion of the patient-specific dental matrix to allow for curing of the filling material applied to the targeted tooth and located within an interior opening of the patient-specific dental matrix to be cured by the ultraviolet light transmitted through the patient-specific dental matrix.

17. The method of claim 1, wherein the patient-specific dental matrix includes an aperture configured to receive the targeted tooth such that internal surfaces of the patient-specific dental matrix are shaped to conform to unique contours of the targeted tooth and surrounds the targeted tooth by engaging the four surfaces of the targeted tooth.

18. The method of claim 1, further comprising:
curing the filling material applied to the targeted tooth;
removing the dental matrix from the targeted tooth after curing the filling material.

* * * * *

UNITED STATES PATENT AND TRADEMARK OFFICE
CERTIFICATE OF CORRECTION

PATENT NO. : 10,357,334 B2
APPLICATION NO. : 14/140836
DATED : July 23, 2019
INVENTOR(S) : Lindsay Hegland Page 1 of 1

It is certified that error appears in the above-identified patent and that said Letters Patent is hereby corrected as shown below:

On the Title Page

In Column 2 (Abstract), Line 2, delete "in in" and insert --in--, therefor.

In the Claims

In Column 19 Line 59, In Claim 2, before "of" delete "opening", therefor.

In Column 20 Line 1, In Claim 3, delete "curved," and insert --curved--, therefor.

In Column 20 Line 7, In Claim 4, delete "the," and insert --the--, therefor.

Signed and Sealed this
Tenth Day of September, 2019

Andrei Iancu
*Director of the United States Patent and Trademark Office*